United States Patent [19]

Ziegler et al.

[11] Patent Number: 5,232,688
[45] Date of Patent: Aug. 3, 1993

[54] SELF-TANNER COSMETIC COMPOSITIONS

[75] Inventors: Philip D. Ziegler, Oxford; Brian A. Crotty, Branford, both of Conn.

[73] Assignee: Chesebrough-Pond's USA Co., Division of Conopco, Inc., Greenwich, Conn.

[21] Appl. No.: 899,403

[22] Filed: Jun. 17, 1992

[51] Int. Cl.$^5$ .................. A61K 7/42; A61K 7/021
[52] U.S. Cl. ........................... 424/59; 424/63; 424/401
[58] Field of Search .............. 424/63, 59; 514/675, 514/693, 698

[56] References Cited

U.S. PATENT DOCUMENTS

| 3,895,104 | 7/1975 | Karg | 424/47 |
| 4,434,154 | 2/1984 | McShane | 424/60 |
| 4,940,577 | 7/1990 | Greenberg | 514/941 |

FOREIGN PATENT DOCUMENTS

61950/90 3/1991 Australia .

OTHER PUBLICATIONS

J. Soc. Cosmet. Chem., 35, pp. 265-272 (Aug. 1984) (Bobin et al.).
Agric. Biol. Chem., 44 (7), pp. 1595-1599 (Kawashima et al.).

Primary Examiner—Thurman K. Page
Assistant Examiner—Sally Gardner
Attorney, Agent, or Firm—Milton L. Honig

[57] ABSTRACT

A composition and method for self-tanning of skin is provided which includes an α-hydroxy substituted ketone or aldehyde such as dihydroxyacetone, a polyacrylamide and a pharmaceutically acceptable carrier. Advantageously, there may also be incorporated at least 15% propylene glycol to improve color intensity.

6 Claims, No Drawings

SELF-TANNER COSMETIC COMPOSITIONS

BACKGROUND OF THE INVENTION

1. Field of the Invention

The invention concerns a cosmetic composition which imparts a tan similar in color to a natural suntan onto the skin.

2. The Related Art

Today there is a great health concern with natural tanning through sunlight. Ultraviolet radiation from the sun is considered to be a leading factor in causing skin cancer. Even if not lethal, ultraviolet radiation has been acknowledged as accelerating aging and wrinkling processes on the skin.

Beyond health concerns, there are obvious practical reasons against natural tanning. Foremost is the reason that in many areas of the globe and during all but summertime, there is insufficient sunlight available to accomplish a natural tan.

Based on the above considerations, there has been much interest in effectuating a tan through cosmetic means. Dihydroxacetone (hereinafter known as DHA) has widely been utilized in cosmetics to accomplish self-tanning of the skin. In the *J. Soc. Cosmet. Chem.*, 35, pages 265–272 (August 1984), Bobin et al. studied the Maillard reaction of DHA with various amino acids found naturally in the hydrolipid film and first layers of the stratum corneum. The Maillard reaction method has commonly been utilized as an artificial tanning system since 1960.

Other studies on the Maillard reaction between DHA and amino acids have been reported in *Agric. Biol. Chem.*, 44 (7). pages 1595–1599 (Kawashima et al.). Through this study it was determined that the rate of browning was maximum around a DHA-amino acid molar ratio of 1.5 when the total concentration of both reactants together was constant at 0.1M. Lysine and glycine were found to have the highest browning activity.

Another approach to the tanning problem is reported in Australian Patent 61950/90 to L'Oreal. The art had earlier appreciated that both DHA and 5,6-dihydroxy indole and certain of its derivatives would each independently cause coloration in the skin; the mechanisms were each believed to be different. The Australian patent teaches that a combination of these materials achieves a rapidly developed intense coloration much closer to the hue imparted by natural tanning than the colorations obtained with each of the compounds taken separately. Since DHA and indole are unstable in the presence of one another, the patent further suggested delivering these compounds from separate compartments of a multi-compartment kit.

Although there has been great progress in sunless self-tanning compositions as noted above, considerable further progress is needed to increase speed of coloration and achieve a coloration even closer to a natural tan. For medical safety reasons, it is also preferred to avoid use of indoles. Furthermore, many of the known self-tanning compositions have storage stability problems. DHA can rapidly decompose in many streaking is a still further problem faced by the art. By the term "streaking" is meant noneven deposition on the skin; the tan coloration tends to migrate along an outer perimeter as a result of the formula being rubbed around upon the skin.

Accordingly, it is an object of the present invention to provide a composition and method for self-tanning having improved rates of coloration and imparting a more natural hue.

A further object of the present invention is to provide a composition and method for self-tanning which utilizes ingredients that impart good aesthetics and have an impeccable health safety profile.

A still further object of the present invention is to provide a composition and method for self-tanning which utilizes mutually compatible ingredients that do not decompose upon storage.

Still another object of the present invention is to provide a composition and method for self-tanning which avoids the streaking phenomena.

These and other objects of the present invention will become more readily apparent through the following summary, detailed discussion and Examples which follow.

SUMMARY OF THE INVENTION

A cosmetic composition is provided comprising:
(i) from about 0.1 to about 40% by weight of a $C_3$–$C_{24}$ α-hydroxy substituted ketone or aldehyde;
(ii) from about 0.1 to about 20% by weight of a polyacrylamide; and
(iii) an effective amount of a pharmaceutically acceptable vehicle for delivering components (i) and (ii) to skin.

A method is also provided for imparting a natural-appearing, nonstreaking tan to skin comprising the delivery and spreading of the aforementioned cosmetic composition onto the skin.

DETAILED DESCRIPTION OF THE INVENTION

Now it has been discovered that a natural appearing self-tan of improved color intensity and nonstreakiness can be achieved by delivering to the skin a combination of a $C_3$–$C_{24}$ α-hydroxy substituted ketone or aldehyde along with a polyacrylamide.

According to the invention the $C_3$–$C_{24}$ α-hydroxy substituted ketone or aldehyde will be present in an amount from about 0.1 to about 40%, preferably from about 1 to about 20%, optimally between 2 and 15 by weight.

The α-hydroxy substituted ketone or aldehyde may be selected from dihydroxacetone, glucose, xylose, fructose, reose, ribose, pentose, arabinose, allose, tallose, altrose, mannose, galactose, lactose, sucrose, erythrose, glyceraldehyde and combinations thereof. Most preferred is dihydroxacetone.

A critical second component is that of an polyacrylamide. This substance serves the dual purpose of thickening the composition while simultaneously providing for nonstreaking performance on skin. Polyacrylamide also much improves low odor maintenance. Other thickeners such as Carbopol ®type polyacrylates when combined with DHA produced malodor and/or browning of the composition. The preferred polyacrylamide according to the present invention is available under the trademark Sepigel 305 ® from Seppic, Inc., Fairfield, New Jersey. Small amounts of a $C_3$–$C_{14}$ isoparaffin and Laureth-7 are present alongside the polyacrylamide in Sepigel 305 ®. Molecular weight of the polyacrylamide may range anywhere from 1000 up to 5,000,000. Preferably the polyacrylamide is a crosslinked polyacrylamide. Amounts of the polyacrylamide will range from 0.1 to about 20%, preferably between about 1 and 10%, optimally between about 1.5 and 3% by weight.

Advantageously, there may also be incorporated propylene glycol at levels of at least 15% preferably between about 25 and 90%, optimally between about 25 and 45% by weight. Propylene glycol at these high levels was found to improve color intensity on the skin when combined with dihydroxacetone. Especially preferred is a combination of dihydroxacetone and propylene glycol in a weight ratio from about 2:1 to about 1:50. Preferably the weight ratio may range from about 1:1 to about 1:10, optimally about 1:8.

While dyes such as indole derivatives may be incorporated into the composition, for health and performance reasons, it may be desirable to formulate in the absence of indole derivatives.

A wide variety of pharmaceutically acceptable vehicles may be utilized for the present invention.

Water is a preferred vehicle or carrier for the compositions of this invention. The amount of water may range from about 5 to about 95%, preferably from about 30 to about 80%, optimally between about 40 and 70% by weight.

Contemplated within the scope of this invention are water-in-oil emulsions in the form of lotions and creams. Oil advantageously is the continuous phase. The amounts of the oil to water phases may range from about 2:1 to 1:100, preferably about 1:1 to 1:10.

Among other types of pharmaceutically acceptable vehicles may be silicone oils. Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients.

Silicones may be present in amounts ranging from about 0.1 up to about 60%, preferably from about 2 to about 25%, optimally between about 10 and 20% by weight.

Synthetic esters are a further category of possible pharmaceutically acceptable vehicles which can also be utilized as emollients within compositions of the invention. Among the suitable esters are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$-$C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Compositions of the present invention may also include emulsifiers or surfactants which may be of the nonionic, anionic, cationic or amphoteric type. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono and di-fatty acid esters of ethylene glycol wherein the fatty acid moiety contains from 10 to 20 carbon atoms, fatty acid monoglyceride wherein the fatty acid moiety contains from 10 to 20 carbon atoms, polyoxyethylene sorbitol, polyoxypropylene sorbitan, and hydrophilic wax esters. Amounts of the emulsifier may range anywhere from about 0.1 to about 20% by weight of the composition, preferably from about 2 to about 10% by weight.

Among other skin benefit agents which may be present in the compositions of this invention are fatty acids and alcohols having from 10 to 20 carbon atoms. Suitable examples of the fatty acids include pelargonic, lauric, myristic, palmitic, stearic, isostearic, hydroxystearic, oleic, linoleic, ricinoleic, arachidic, behenic, and erucic acids. Examples of satisfactory fatty alcohols include lauryl, myristyl, cetyl, hexadecyl, stearyl, isostearyl, hydroxystearyl, oleyl, ricinoleyl, behenyl, erucyl, and 2-octyl dodecanyl alcohols. These materials may be present in amounts anywhere from about 0.1 to about 20% by weight of the composition.

A sunscreen agent is a further desirable ingredient of the compositions of this invention. The term "sunscreen agent" as used herein defines ultraviolet ray-blocking compounds exhibiting absorption within the wavelength region between 290 and 400 nm. Sunscreens may be classified into five groups based upon their chemical structure: para-amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide and polymer particles such as those of polyethylene and polyamides. Preferred materials include p-aminobenzoic acid and its derivatives, anthralinates; salicylates; cinnamates; courmarin derivatives; azoles; and tannic acid and its derivatives.

Preservatives can desirably be incorporated into the cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of parahydroxybenzoic acid. Other preservatives which have more recently come into use include hydantoin derivatives, proprionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol (phenoxetol), methylparaben, imidazolidinyl urea, sodium dehydroxyacetate, propylparaben, trisodium ethylenediamine tetraacetate (EDTA) and benzyl alcohol. The preservative should be selected having regard for possible incompatibilities between the preservative and other ingredients. Preservatives are preferably employed in amounts ranging from about 0.01% to about 2% by weight of the composition.

Minor adjunct ingredients may also include fragrances, antifoam agents, opacifiers (e.g. titanium dioxide) and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

The following formula is typical of compositions according to the present invention.

| Ingredient | Wt. % |
|---|---|
| Deionized Water | 66.4470 |
| Propylene Glycol | 25.0000 |
| Pecosil PS-100 | 1.0000 |
| Dihydroxyacetone | 3.0000 |
| Sepigel 305 | 2.3744 |
| Diglycerin | .5000 |
| Glycerin | .5000 |
| Sodium Hydroxide | .3032 |

-continued

| Ingredient | Wt. % |
|---|---|
| Phenoxetol | .3000 |
| Methylparaben | .2000 |
| Fragrance | .2000 |
| Propylparaben | .1000 |
| Titanium Dioxide | .0750 |

EXAMPLE 2

A series of experiments were conducted to evaluate the effect of various glycols on the color reaction with 3% dihydroxacetone. These experiments are reported in Table I below.

TABLE I

Color Intensity Imparted on Skin by DHA with Solvent

| Polyols | | Color Intensity |
|---|---|---|
| 25% | Glycerin | ++ |
| 25% | Carbowax 200 | ++++ |
| 25% | Carbowax 200 | ++++++ |
| 12.5% | Propylene Glycol | |
| 12.5% | Propylene Glycol | +++ |
| 7.5% | Carbowax | +++++ |
| 12.5% | Propylene Glycol | |
| 22.5% | Propylene Glycol | +++++ |
| 25% | Propylene Glycol | ++++++ |
| 45% | Propylene Glycol | +++++++++ |
| 48% | Butylene Glycol | +++++ |
| 25% | Diethylene Glycol Monoethyl Ether | +++ |
| Others | | |
| 45% | Acetamide MEA | + |
| 45% | Lactamide MEA | No color |

Based on the results listed in the Table, it is evident that propylene glycol has a color enhancing interaction with dihydroxyacetone. Other glycols such as glycerine, butylene glycol and diethylene glycol monoethyl ether were operative but not to the same extent as propylene glycol. Levels of 45% propylene glycol were much more effective than lower levels.

The foregoing examples illustrate only selected embodiments of the present invention and should be considered nonlimiting examples with variations and modifications thereof all being within the spirit and purview of this invention.

What is claimed is:

1. A cosmetic composition comprising:
   (i) from about 0.1 to about 40% weight of a $C_3$–$C_{24}$ α-hydroxy substituted ketone or aldehyde which is selected from the group consisting of dihydroxacetone, glucose, xylose, fructose, reose, ribose, pentose, arabinose, allose, tallose, altrose, mannose, galactose, lactose, sucrose, erythrose, glyceraldehyde and combinations thereof;
   (ii) from about 1 to about 20% by weight of a polyacrylamide; and
   (III) from about 5 to about 95% by weight of a pharmaceutically acceptable vehicle for delivering components (i) and (ii) to skin.

2. The composition according to claim 1 wherein the α-hydroxy substituted ketone is dihydroxacetone.

3. The composition according to claim 2 further comprises at least 15% by weight propylene glycol.

4. The composition according to claim 3 wherein dihydroxyacetone and propylene glycol are present in a weight ratio from about 2:1 to about 1:50.

5. The composition according to claim 4 wherein propylene glycol is present in an amount from about 25% to about 45% by weight.

6. A method for imparting a natural-appearing, non-streaking tan to skin comprising applying to the skin a composition according to claim 1.

* * * * *